United States Patent [19]

Eppelmann et al.

[11] Patent Number: 4,879,917

[45] Date of Patent: Nov. 14, 1989

[54] APPARATUS FOR DETERMINING THE ACTIVE INGREDIENT RELEASE FROM SOLUBLE PHARMACEUTICAL PRODUCTS

[76] Inventors: Heinz Eppelmann, Johannes-Calvin-Str. 15, D-6507, Ingelheim; Franz Fahler, Birkenwaldstr. 35, D-6053, Obertshausen, both of Fed. Rep. of Germany

[21] Appl. No.: 152,923

[22] Filed: Feb. 5, 1988

[30] Foreign Application Priority Data

Feb. 6, 1987 [DE] Fed. Rep. of Germany ....... 3703621

[51] Int. Cl.⁴ ............................................. G06F 15/46
[52] U.S. Cl. ........................................ 73/866; 366/343
[58] Field of Search ................. 73/866, 53; 15/24, 29; 366/342, 343

[56] References Cited

U.S. PATENT DOCUMENTS

| | | | |
|---|---|---|---|
| 1,584,740 | 9/1924 | Denny | 15/24 |
| 3,791,222 | 2/1974 | Goodhart et al. | 73/53 |
| 3,802,272 | 4/1974 | Bischoff et al. | 73/866 |
| 4,335,438 | 6/1982 | Smolen | 73/866 |

*Primary Examiner*—Stewart J. Levy
*Assistant Examiner*—Michele Simons
*Attorney, Agent, or Firm*—Robert J. Koch

[57] ABSTRACT

A dissolution rate analyzer for determining the solubility of pharmaceutical products. It automatically loads, mixes, and samples the test product; then cleans and dries the test vessel before repeating the process. The analyzer has a plurality of vessels with agitator blades. Each blade has a series of channels and is attached to a hollow shaft which is rotatable and vertically displaceable. The channels in the blades are connected by the hollow shaft with sources of fluid and air. By pumping liquid and air out the channels in the blades, and simultaneously rotating the agitator and moving it up and down, the vessel thoroughly cleans itself. The cleaning liquid is drained off through a valve in the bottom of the test vessel. A magazine connected to a dispenser loads the next sample, fluid is added, and the mixture is agitated before analysis of the next sample begins.

8 Claims, 6 Drawing Sheets

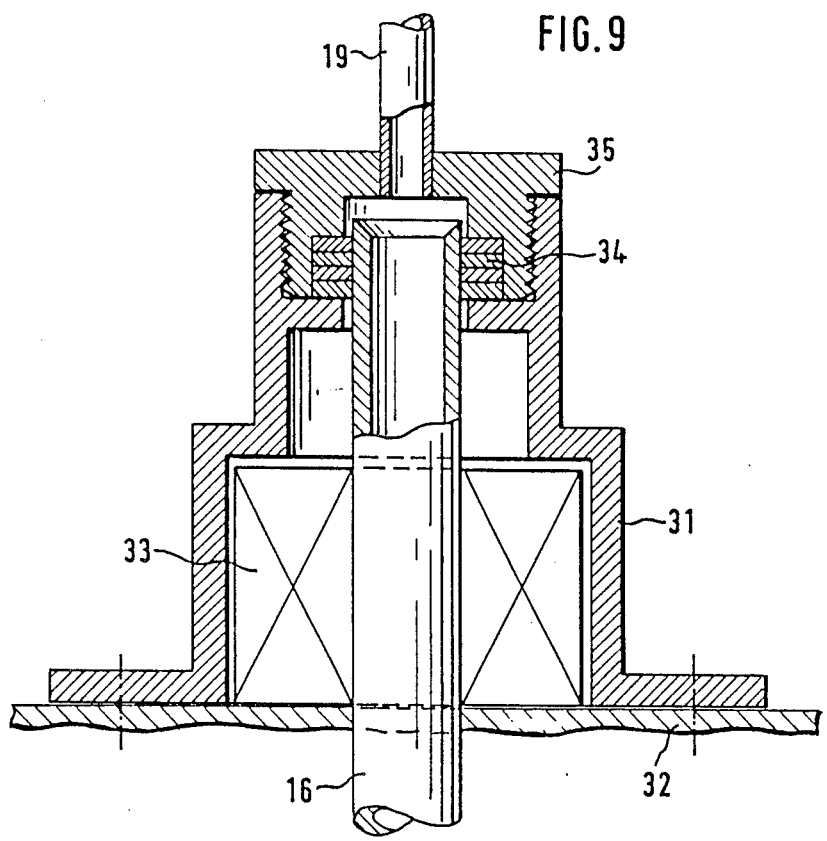

4,879,917

APPARATUS FOR DETERMINING THE ACTIVE INGREDIENT RELEASE FROM SOLUBLE PHARMACEUTICAL PRODUCTS

BACKGROUND OF THE TECHNOLOGY

The invention concerns an apparatus for the determination of the release of active ingredients by soluble pharmaceutical products. These products may be in forms suitable for oral administration, in particular tablets, pills, capsules and beads. The inventive apparatus comprises a plurality of vessels located in a stand and equipped with a vertically-moving, centrally-driven agitator for each vessel. The apparatus also has means for filling and emptying the vessels of the appropriate liquids.

The testing for active ingredient release involves testing medicines under controlled and constant conditions. These conditions include the test temperature, agitator velocity, analysis intervals and other parameters. Such investigations are described and specified in national standards for Germany (DAB: Deutsches Arzneibuch—German Pharmacopeia) and international specifications, for example the USP (US Pharmacopeia) and BP (British Pharmacopeia). Such tests are an important evaluation criterion during the development of these drugs in addition to ongoing quality control. At least six samples are to be investigated simultaneously under constant conditions. The number of samplings may range from one to more than twenty.

The determination of the release of active ingredients from solid and soluble pharmaceutical products is a particularly labor-intensive and time-consuming activity in pharma-analytical laboratories.

The test specifications cited above contain detailed descriptions of the apparatus to be used. The apparatus appearance, size, construction materials, agitator configuration, and tolerances to be observed in the essential components are all set forth.

Devices are known for making release rate determinations and which satisfy the aforementioned specifications. The active ingredient release apparatus PTW 12 S of the Pharmatest GmbH Co., D-6452 Hainburg is one such apparatus.

The Pharmatest PTW 12 S apparatus consists essentially of a row of vessels. Each vessel is equipped with a centrally-driven agitator. The vessels are essentially cylindrical and have a hemispherical bottom. Charging, sampling, and cleaning are effected manually from the open top of the cylinder. This manual operation is not efficient and leads to avoidable interferences. For example, the vessels are cleaned in succession. This sequence requires considerable time.

SUMMARY OF THE INVENTION

It is an objective of the invention to fully automate the necessary operations and improve the efficiency. In particular, it is an objective to improve the charging, cleaning, and sampling of the apparatus whereby the efficiency of the testing process may be considerably improved.

These objectives are attained by using an apparatus comprising:

(a) a central control, drive and charging unit associated with a stand, a pumping unit and at least one mixing vessel;

(b) a valve in the bottom of each vessel which can be automatically actuated to open and close by a central control unit;

(c) a tubular or hose connection attached to each vessel, said tube or hose in turn being connected with a central pump or vacuum pump installation; and (d) an agitator extending into each vessel and comprising an agitator body connected with an agitator shaft having the form of a hollow pipe, wherein said agitator body comprises a plurality of channels connected with the hollow pipe which channels extend on or in the agitator body to the outer edge of the agitator body surface, said channels having free outlets.

In a further embodiment, the stand has an upper part capable of a lifting and lowering motion. The agitator shafts of the agitator bodies pass through the stand by means of a pivot bearing so that the agitator shafts may also rotate and entrain material while moving vertically.

Advantageously, a motor driven belt drive is provided in the upper part of the stand and is connected to each of the agitator shafts. At least one belt pulley is used for engaging the belt drives and to effect the agitator rotation.

According to the invention, a valve is attached to an opening in the bottom of a vessel. The valve comprises an olive-shaped connecting piece. This connecting piece comprises: (a) in its lower part, a sleeve having at least one opening, and (b) a stopper urged upwardly by a spring into the vessel bottom opening, said stopper being located in said sleeve and vertically displaceable therein.

Each agitator body is advantageously in the form of a blade agitator having hollow channels extending across the blade. A hollow agitator shaft connects the agitator blade (and its channels) with a connector for introducing air or liquid down through the shaft and into the vessel through the blade channels. This fluid passage permits the vessel to be completely cleaned by introducing liquids into the vessel through the blade channels as the blades rotate and/or move vertically. Water is a preferred cleaning liquid.

The used cleaning fluid may be removed by an automatic valve in the bottom of the vessel. Air may then be blown through the blades to dry the vessel for reuse. Because the cleaning and drying operations may be carried out simultaneously for all vessels, the entire device is ready for use within a very short time.

In a further embodiment of the invention, at least one tablet magazine is associated with the stand. It is also possible to provide each vessel with its own tablet magazine, so that special feeding devices are not needed. In other cases, the apparatus should be provided with displaceable rails extending over the length of the stand or individual rails which automatically supply each vessel with samples.

The vessels are modified and laid out so that all test steps are performed simultaneously and automatically. Test sample introduction, testing, rinsing, and drying are performed more efficiently than previously. An apparatus of this type may be completely controlled and monitored by means of a computer whereby records may also be generated and maintained.

BRIEF DESCRIPTION OF THE DRAWINGS

The invention will become more apparent from the figures attached hereto, wherein:

FIG. 2a shows a front elevation of the measuring and pump unit of FIG. 1 at a slightly larger scale;

FIG. 2b shows a lateral elevation of the measuring apparatus according to FIG. 2a;

FIG. 2c shows a top view of the measuring apparatus of FIG. 1;

FIG. 9 shows the upper part of an agitator shaft.

DETAILED DESCRIPTION OF THE INVENTION

In the figures, identical elements are designated by the same reference symbols.

Figure 1:
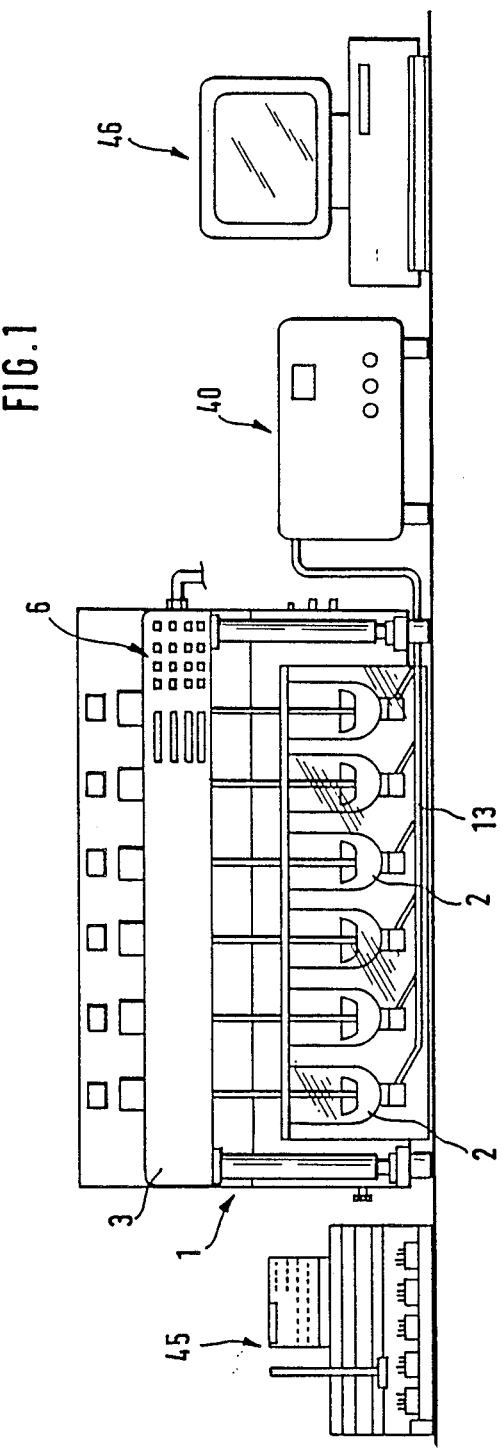
FIG. 1 shows a front elevation of the entire system with a sample collector, a measuring apparatus according to the invention, a pump unit, and a control computer.

FIG. 1 presents an overview of the entire measuring system. The central unit is the measuring apparatus with its stand 1 and vessels 2 for dissolving the samples.

A keyboard unit 6 is provided on the front of section 3 for operating the measuring apparatus and automatic controls. Upper section 3 contains the drive for the agitators in vessels 2. A collector line 13 connects individual vessels 2 with pumping unit 40. Unit 45 designates a sample collector or spectral photometer, whereby the analysis and evaluation of the results of the measuring apparatus are carried out. The specifics of unit 45 are not part of the present invention. The same is true for computer 46 used to control the entire system.

Figure 2:
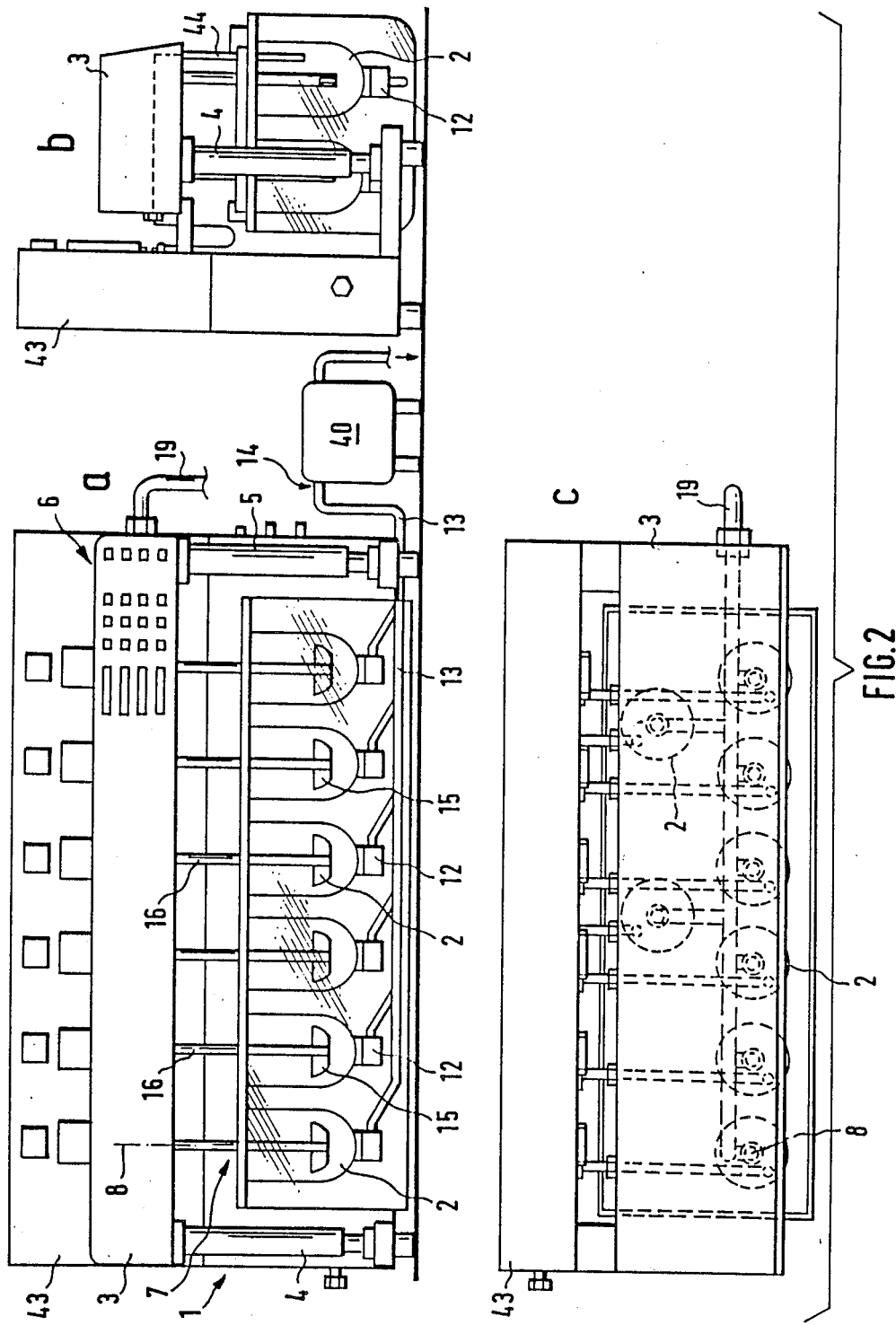

FIGS. 2a, 2b and 2c show the measuring apparatus in a front, lateral and top elevation at a slightly enlarged scale relative to FIG. 1. As depicted, stand 1 contains eight vessels 2. Upper section 3 may be moved up and down by means of pistons 4 and 5 (FIG. 2a).

The top ends of agitators 7 are supported in upper section 3 and extend into vessels 2 terminating in agitator blades 15. The top support allows hollow agitator shafts 16 to rotate and move vertically.

Each vessel 2 is equipped with a valve 12 that may be actuated automatically and which will be described in more detail in connection with FIG. 5. Valve 12 is located in the bottom of each vessel 2. Each valve 12 is connected by means of a hose line 13 with a pumping unit 40 which may be a suction pump.

Figure 3:
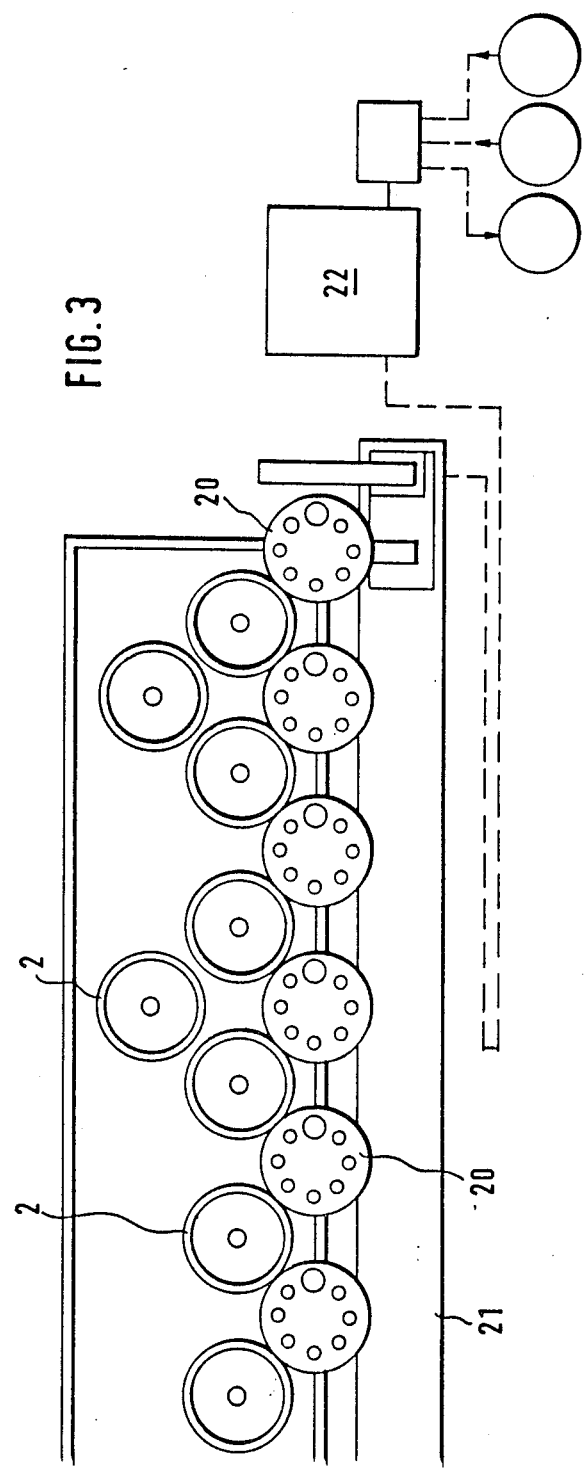
FIG. 3 shows a top view of a measuring apparatus equipped with sample supply means.

FIG. 3 further shows tablet magazine 20 for automatically charging vessels 2. Magazine 20 transfers the tablets to an inserting rail 21. Rail 21 is displaceable along stand 1 so that tablets deposited on rail 21 may be dropped into vessels 2.

By means of appropriate holes in inserting rail 21, vessels 2 of the same line may be charged simultaneously. The control unit 22 controls the entire operation of charging, emptying and cleaning of vessels 2.

The function of control unit 22 may be taken over by computer 46 (FIG. 1).

In operation, agitator shafts 16 must be rotated during the testing phase and moved vertically during the cleaning phase. The blades may also be rotated during the cleaning.

Figure 4:
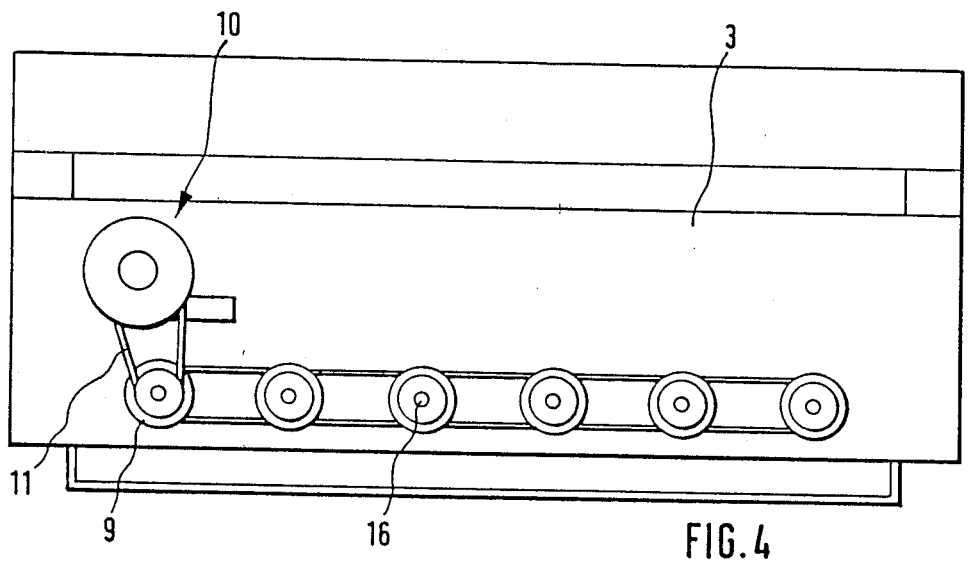
FIG. 4 shows a top view of a measuring apparatus in a longitudinal section through the upper part with the drive.

Reference is made here to FIG. 4 which shows a top view through upper section 3. This embodiment contains only six vessels 2 while all of the above-described means and functions are similar.

The top ends of agitator shafts 16 are equipped with a drive gear 9 to effect a rotating motion. Drive gear 9 is driven by drive belt 11 directly or indirectly connected with motor 10. Because the drive mechanism is located in upper section 3, the drive mechanism takes part in the lift motion and makes possible a simultaneous rotation of agitator shafts 16. The specific configuration of agitator body 15, which will be described later relative to FIG. 6, can therefore be moved along the inner wall of vessels 2 and carry out the cleaning operation in a fully automatic manner.

Figure 5:
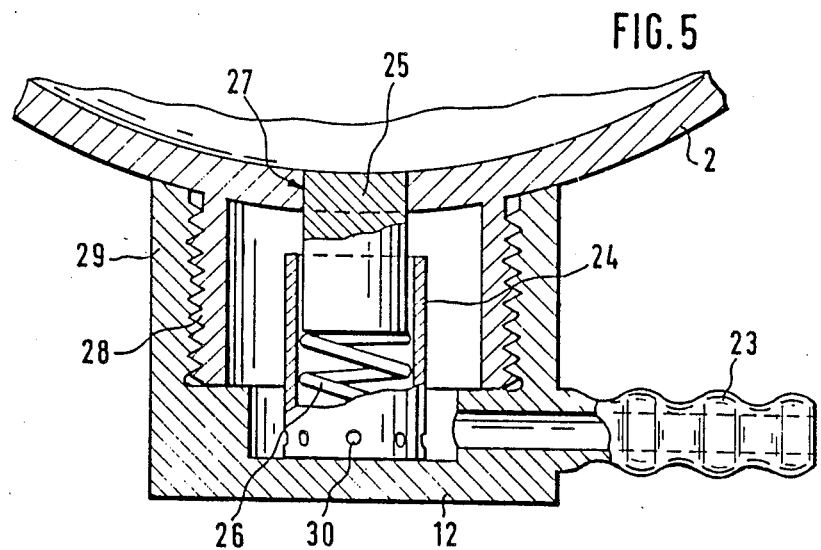
FIG. 5 shows a view enlarged relative to FIGS. 1 to 4 of the lower part of a vessel with an automatic valve attached thereto.

FIG. 5 shows an enlarged section of the bottom of a vessel 2 with a built-in valve 12 for the automatic opening and closing of vessel 2.

An outer thread 28 is fixedly joined to the bottom of vessels 2. A valve housing 29 is fixedly and tightly screwed onto thread 28, said housing being equipped with an olive-shaped nipple 23 as a connecting part. In place of olive-shaped nipple 23, a cylindrical piece of pipe may also be used.

In valve housing 29, a guide sleeve 24 provided with lateral openings 30 is coaxially mounted. Guide sleeve 24 partially surrounds the freely displaceable stopper 25, which is pressured by spring 26 into opening 27 of the vessel bottom, in the absence of an external effect. In place of the pressure controlled valve 12, a magnetic valve (not shown) may also be used.

The mode of operation of the valve follows from the aforedescribed configuration.

After completing the active ingredient release determination, a vacuum is created at olive-shaped nipple 23 by pumping unit 40 connected at this point. (The pump may be a water jet pump.) The vacuum produced in this manner draws stopper 25 downward against the pressure of spring 26 thereby unblocking opening 27 in the bottom of vessel 2. The medium in vessel 2 is drawn through opening 27, nipple 23, pump inlet 14 and pump 40 into a drainage vessel (not shown). Pumping unit 40 is deactivated when drainage is complete. Spring 26 then presses stopper 25 into opening 27, thereby closing vessel 2. A thorough cleaning of vessel 2 follows as described below.

Figure 6:
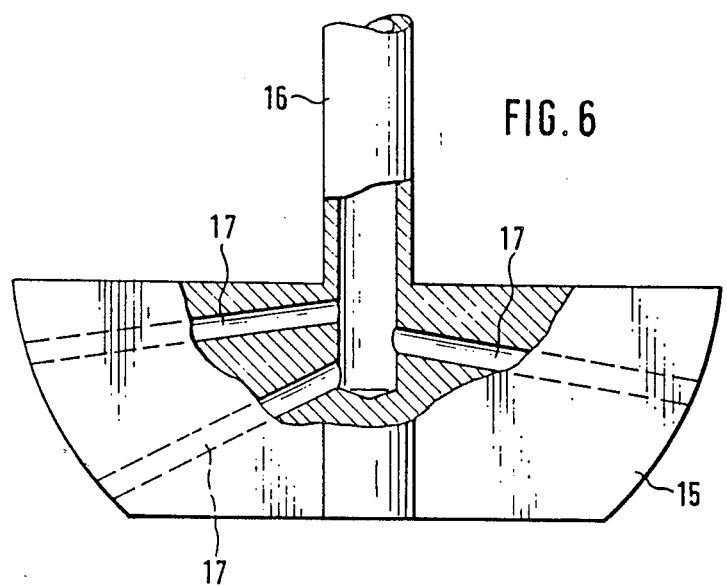
FIG. 6 shows a longitudinal section through an agitator body at the scale of FIG. 5.

FIG. 6 illustrates the lower part of agitator 7 comprising hollow shaft 16 and agitator body 15. Agitator body 15 comprises a blade agitator through which pass a plurality of essentially radical channels 17. These channels are fluidically connected with the hollow pipe of agitator shaft 16. If cleaning liquid is introduced in a controlled manner into agitator shaft 16 through connector fitting 19 and agitator 7 is rotated together with its agitator body 15, the centrifugal force acting on the liquid already present in channels 17 sprays the liquid against the inner walls of vessel 2. If a lifting motion is added simultaneously, all of the inner parts of the wall may be reached by cleaning liquid ejected. An adequately vigorous liquid spray can be produced with a variable pressure so that complete cleaning is assured.

During the introduction of cleaning fluid, stopper 25 remains in its blocking position so that vessel 2 is filled and agitator body 15 itself cleaned. Subsequently, the rinsing liquid is removed through opening 27 in the bottom of vessel 2 and the cleaning process may be repeated if necessary. Finally, vessel 2 and agitator 7 are dried by means of compressed air blown through agitator 7.

After vessel 2 has been cleaned and dried, the medium into which the release occurs may be delivered into vessel 2 and adjusted for temperature. Following the attainment of a constant temperature, the test object (e.g., a tablet) may be inserted into the medium for automatically testing the release of the active ingredients.

Figure 7:
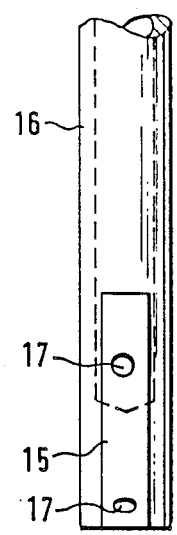
FIG. 7 shows a top view of the left hand part of the blade agitator of FIG. 6.

FIG. 7 is a bottom elevation of the left part of agitator body 15 according to FIG. 6 and shows both of the openings of channels 17.

Figure 8:
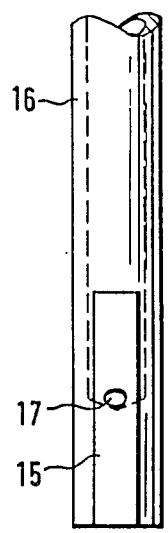
FIG. 8 shows a top view of the right hand part of the blade agitator of FIG. 6.

FIG. 8 shows a top view from below of the right part of agitator body 15 with one of the openings of channel 17 according to FIG. 6. As seen relative to this in FIG. 6, the openings of channels 17 are effectively distributed over the opposite wall of vessel 2 over the height of agitator body 15 in a uniform manner, without detrimentally affecting the mechanical configuration of agitator body 15.

In FIG. 9, the upper part of agitator shaft 16 and its surroundings are shown in a vertical section along the center axis. Housing 31 is located above drive part 32 and surrounds the upper end of agitator shaft 16, counter nut 33 and shaft seals 34. Seals 34 are secured from the top by screw 35. Screw 35 is equipped with connector piece 19 through which liquid, preferably water, or air is supplied to agitator body 15.

Sampling is carried out by means of hose pumps wherein the sampled solutions are moved to sample collector 45 by sampling conduit 44 (FIGS. 1 and 2b).

For automation, additional electric or magnetic valves are used to control compressed air, water supply and vacuum generation. All of the functions of the modified release apparatus are controlled by microcomputer 46 so that manual operations are restricted to the setting of the parameters prior to the onset of the test series and the feeding of the test material to the transport rail.

Because all work processes take place simultaneously relative to individual vessels 2, considerable harmonization and economics of the entire measuring system are attained.

We claim:

1. Apparatus for determining the release of active ingredients of soluble pharmaceutical products, said apparatus comprising:
    (a) a stand having an upper section and a connector for air and liquid positioned in said upper section;
    (b) at least one vessel disposed within said stand and positioned beneath said upper section, each vessel having an opening in a lower portion of said vessel and a valve communicating with said opening for emptying liquids contained in said vessel; and
    (c) an agitator at least partially disposed within each vessel, each agitator having a hollow vertical shaft linked to said connector and, said each agitator having an agitator blade having channels extending across said blade to outer edges of said blade and terminating in free outlets, said channels communicating with said hollow vertical agitator shaft.

2. Apparatus as in claim 1 further comprising a suction pump connected to each said valve.

3. Apparatus as in claim 1 wherein said upper section is vertically displaceable and said vertical agitator shaft is bearingly supported within said upper section whereby said vertical agitator shaft can be rotated while being vertically displaced as said upper section is vertically displaced.

4. Apparatus as in claim 1 wherein said upper section further comprises a belt drive connected to each said vertical agitator shaft for rotating said agitator.

5. Apparatus as in claim 1 wherein each of said valves comprises (a) a sleeve coaxially mounted with said opening and having at least one lateral opening, (b) a stopper freely displaceable within said sleeve, and (c) a spring disposed below said stopper and urging said stopper upwardly toward said opening.

6. Apparatus as in claim 9 wherein said agitator is connected to said air and liquid connector whereby said connector is in fluid communication with said channels on said agitator blade.

7. Apparatus as in claim 1 further comprising at least one automatic vessel charging tablet magazine associated with said upper section of said stand.

8. Apparatus as in claim 7 further comprising an inserting rail displaceable along said stand and communicating with said tablet magazine whereby tablets deposited on said rail from said tablet magazine are displaced and delivered to each vessel.

* * * * *